United States Patent [19]
Ives

[11] Patent Number: 5,361,773
[45] Date of Patent: Nov. 8, 1994

[54] BASAL VIEW MAPPING OF BRAIN ACTIVITY

[75] Inventor: John R. Ives, Lexington, Mass.

[73] Assignee: Beth Israel Hospital, Boston, Mass.

[21] Appl. No.: 985,284

[22] Filed: Dec. 4, 1992

[51] Int. Cl.⁵ .......................................... A61B 5/0476
[52] U.S. Cl. ..................... 128/731; 128/732
[58] Field of Search ................... 128/731–732

[56] References Cited

U.S. PATENT DOCUMENTS

| | | | |
|---|---|---|---|
| Re. 34,015 | 8/1992 | Duffy | 128/731 X |
| 4,498,080 | 2/1985 | Culver | 128/731 X |
| 4,610,259 | 9/1986 | Cohen et al. | 128/731 |
| 4,649,482 | 3/1987 | Raviv et al. | 128/731 X |
| 4,805,625 | 2/1989 | Wyler | 128/642 |
| 4,815,474 | 3/1989 | Duffy | 128/731 |
| 4,862,359 | 8/1989 | Trivedi et al. | 128/731 X |

Primary Examiner—Angela D. Sykes
Attorney, Agent, or Firm—Wolf, Greenfield & Sacks

[57] ABSTRACT

A topographic map and method of mapping brain electrical activity including a first set of points representative of electrical activity occurring in a mesial temporal region of a left brain hemisphere and a second set of points representative of electrical activity occurring in a mesial temporal region of a right brain hemisphere are displayed adjacent and a third set of points representative of electrical activity occurring in a mid-line region of a left brain hemisphere and a fourth set of points representative of electrical activity occurring in a mid-line region of a right brain hemisphere are displayed remote. The respective locations of the first and third sets of points are displayed substantially as a mirror image of the respective locations of the second and fourth sets of points.

26 Claims, 8 Drawing Sheets

BASAL VIEW MAPPING OF BRAIN ACTIVITY

BACKGROUND OF THE INVENTION

1. Field of the Invention

The present invention relates generally to the field of mapping electrical activity of a brain. More particularly, the present invention relates to a topographic map and a method for creating the map in which brain activities occurring in respective temporal lobe regions of a brain are displayed adjacent to each other and brain activities occurring in respective mid-line regions of the brain are displayed remotely.

2. Discussion of the Related Art

Creating topographic maps of brain electrical activity using a set of electrodes disposed on the scalp of a subject is well-known in the art. The electrical topographic map is created by measuring an electric field sensed by each electrode, converting these electric field measurements into processable signals and then locating the processed signals on a two dimensional map. Since the development of brain mapping, the resultant topographic map has always been displayed in a format that corresponds to a top-down or superior view, i.e., looking down on the top of the head.

FIG. 1 shows this basic top-down view 10. A set of electrodes 12i, were i varies from 1 to n is typically placed on the subject's scalp in accordance with the International 10–20 Electrode Placement System. FIG. 1 illustrates the placement of the elementary set of 10–20 electrodes. In the 10–20 electrode system, the patient's scalp is measured and then proportionally divided up in order to place electrodes 12i equally spaced over the scalp. Since the electrodes are equally spaced, the signals sensed by the electrodes can, after processing, be located on the grid of a map. Although occasionally, a flat side view or a three dimensional side view may also be used, the top-down view has been universally accepted as the standard throughout the field of neurophysiology.

The top-down view has several disadvantages. First, if the area of interest for mapping of brain activity is in the temporal lobes, this activity will be located on the outer peripheral edges 14 and 16 of the topographic map. The information so placed becomes less useful diagnostically because it appears to the physician looking at the map that some information may be missing or has been cut off. Furthermore, from a diagnostic perspective, since the majority of focal brain seizures occur in the temporal lobes (approximately 75% of all seizures in epileptic patients, for example) this important diagnostic information is difficult to interpret.

Additionally, information from sphenoidal electrodes has not been adequately incorporated into conventional topographic maps such as the map of FIG. 1. A sphenoidal electrode is a wire which is inserted by a physician into the jaw muscle and nearby tissue to a position near the sphenoid bone where it remains during a test period to sense epileptiform discharges. More specifically, the site of insertion is approximately 3–4 mm below the zygoma and 2–3 cm in front of the tragus and the target is the foramen ovale.

The sphenoidal electrodes are very sensitive to temporal lobe epileptic discharges and often reflect the maximum epileptic electroencephalogram activity. When this important diagnostic information has been used in conventional topographic maps of brain activity, this information has not been anatomically correctly integrated into the top-down topographic map. Anatomically, the sphenoidal electrodes sense brain electrical activity in an area that is substantially directly below the mid-temporal electrodes T3 and T4. Thus, the diagnostic information concerning the mesial part of the temporal lobe as sensed by the sphenoidal electrodes is either not depicted at all or depicted in a way that makes it diagnostically less useful.

Therefore, an object of the present invention is to provide an improved topographic map and method of mapping brain electrical activity that provides enhanced diagnostic information.

Another object of the present invention is to provide an improved topographic map and method of mapping brain electrical activity that permits mapping of the entire surface of the brain in one continuous plane.

SUMMARY OF THE INVENTION

The present invention overcomes the disadvantages of the prior art by providing an improved topographic map and method of mapping brain electrical activity. A first set of points representative of electrical activity occurring in a temporal region of a left brain hemisphere and a second set of points representative of electrical activity occurring in a temporal region of a right brain hemisphere are displayed adjacent to one another and a third set of points representative of electrical activity occurring in a mid-line region of a left brain hemisphere and a fourth set of points representative of electrical activity occurring in a mid-line region of a right brain hemisphere are displayed remote from one another. The respective locations of the first and third sets of points are displayed substantially as a mirror image of the respective locations of the second and fourth sets of points.

The first and second sets of points are derived from electrical activity in the temporal lobe region of the brain. In one embodiment of the invention, the first and second sets of points are respectively derived from electrical activity sensed by at least one sphenoidal electrode disposed proximate a mesial temporal lobe. The third and fourth sets of points may be derived from electrical activity sensed by a set of electrodes located according to an International 10–20 Electrode Placement System.

The topographic map of the present invention may be displayed three dimensionally. Contour lines in shades of gray or different colors may be used to connect points having substantially similar values.

The features and advantages of the present invention will be more readily understood and apparent from the following detailed description of the invention, which should be read in conjunction with the accompanying drawings, and from the claims which are appended at the end of the detailed description.

BRIEF DESCRIPTION OF THE DRAWINGS

In the drawings, which are incorporated herein by reference and in which like elements have been given like reference characters.

DETAILED DESCRIPTION

In contrast to conventional topographic maps of brain electrical activity, the topographic map of the present invention involves "turning" the brain over and mapping from the inferior or basal view, splitting the brain and the corpus callosum, and folding or displaying the two hemispheres out flat in a "filet" or "butterfly" fashion. The entire brain can then be depicted on one plane. The process by which this map is constructed will now be explained.

Figure 2A:
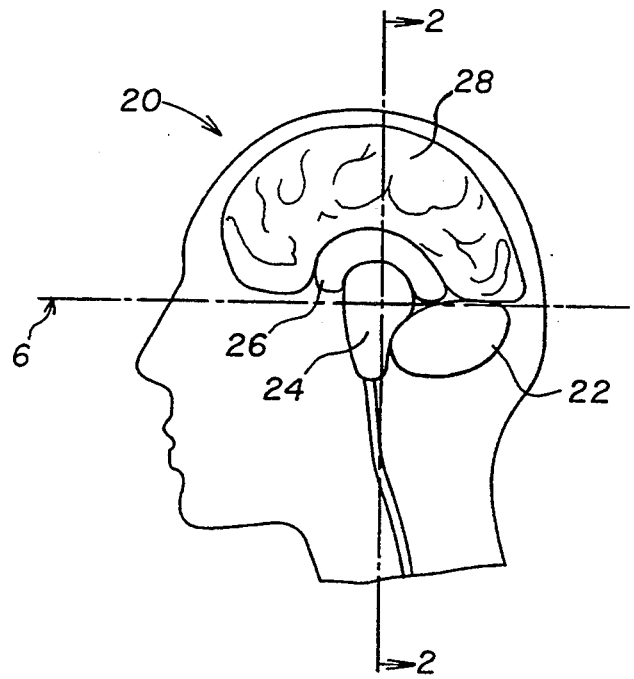
FIGS. 2A and 2B are respective side and cross-sectional views of a subject's head, illustrating mid-line and temporal regions.

FIG. 2A illustrates a cross-section of a brain disposed inside a subject's head 20. The brain typically includes a cerebellum 22, a medulla 24, a corpus callosum 26, and a cerebral hemisphere 28.

Figure 2B:
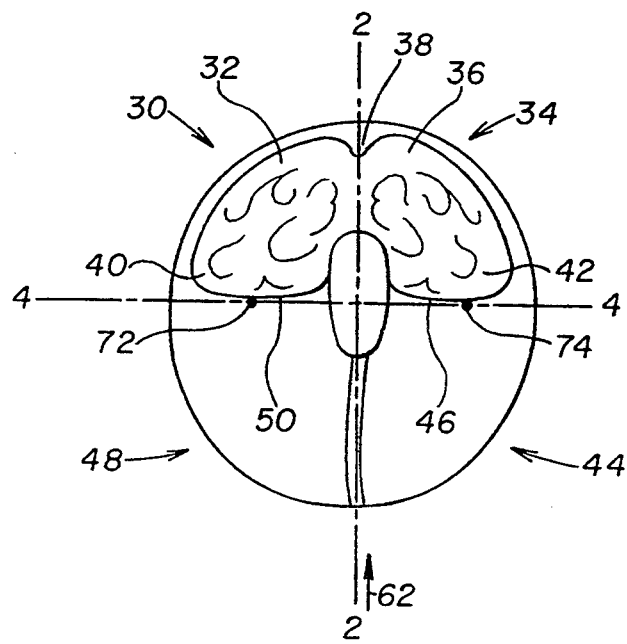

Reference is now made to FIG. 2B, which figure is a cross-section along line 2—2 of the head of FIG. 2A. For analytical purposes, the brain may be divided into four distinct quadrants. A first quadrant 30 defined by lines 2—2 and 4—4 may be termed a mid-line region of a right brain hemisphere 32. A second quadrant 34 also defined by lines 2—2 and 4—4 may be termed a mid-line region of a left brain hemisphere 36. The mid-line regions generally extend from a mid-line 38 to the lateral temporal lobes generally located at 40 and 42, respectively.

A third quadrant 44 defined by lines 2—2 and 4—4 may be termed a temporal region of a left brain hemisphere 42. The third quadrant 44 includes the mesial surface 46 of temporal lobe 42. A fourth quadrant 48, defined by lines 2—2 and 4—4 may be termed a temporal region of a right brain hemisphere 32. The fourth quadrant 48 includes a mesial surface 50 of temporal lobe 40.

Figure 1:
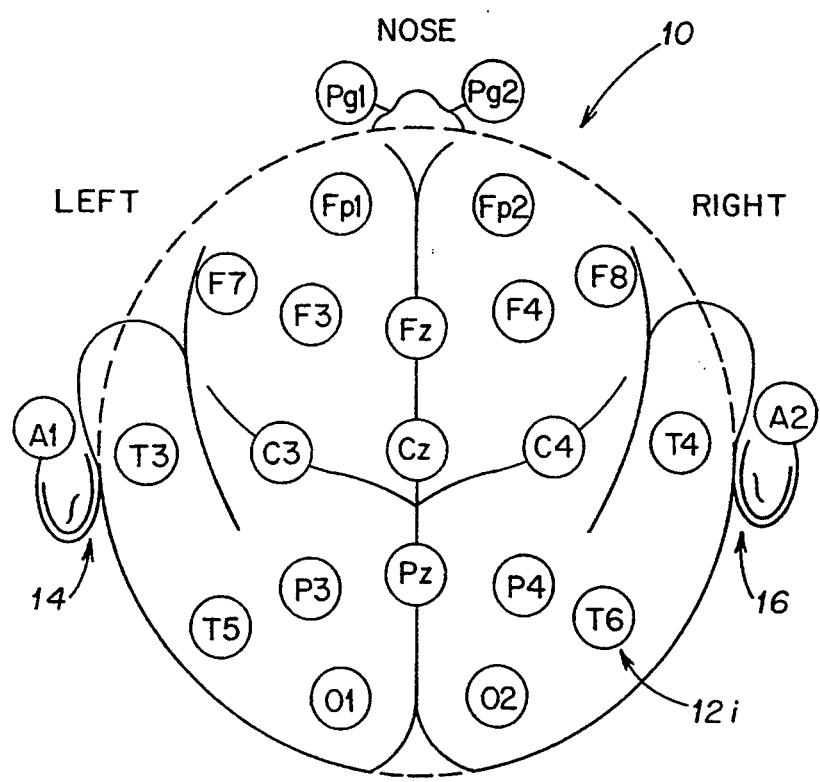
FIG. 1 illustrates a conventional top-down view used in generating topographic maps of brain electrical activity, particularly showing the locations of the elementary set of electrodes in the International 10–20 Electrode Placement System.

A set of electrodes placed on head 20 in accordance with the International 10-20 Electrode Placement System may be used to sense brain electrical activity occurring in mid-line regions 30 and 34 as shown in FIG. 1. A set of electrodes may be used to sense brain electrical activity in the temporal regions 44 and 48. One type of electrode that is useful for sensing activity in the temporal regions is a sphenoidal electrode 72, 74, which is located to sense electrical activity in a mesial temporal lobe surface 50, 46.

Figure 3A:
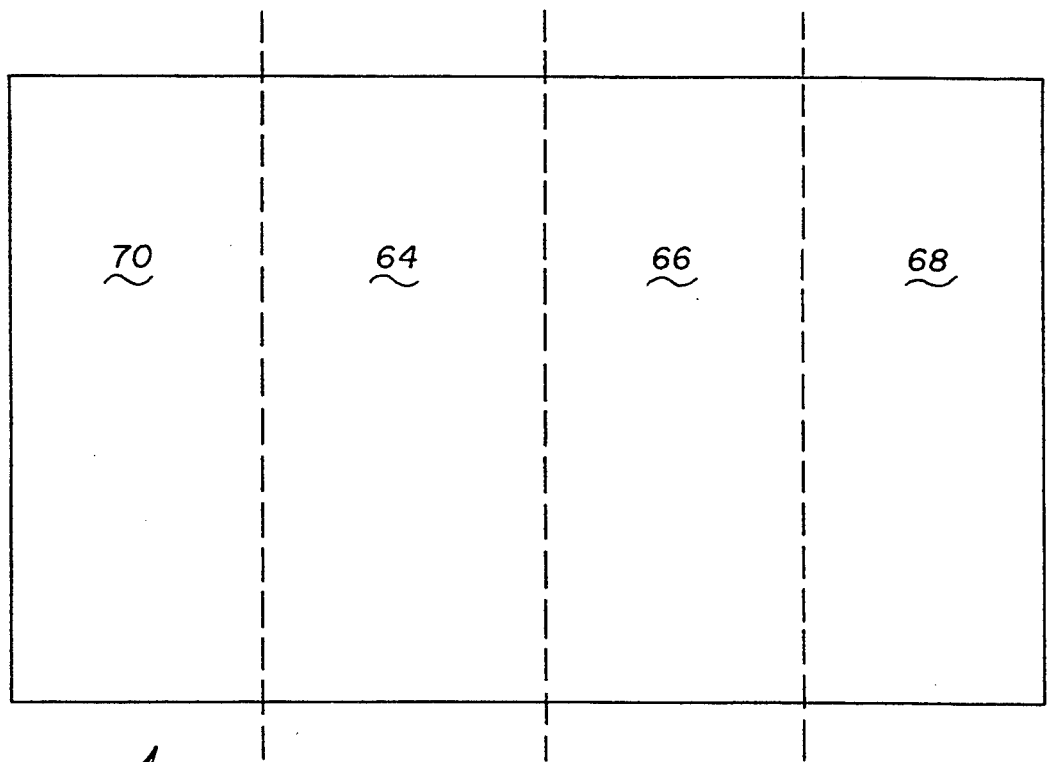
FIGS. 3A, 3B, 3C and 3D illustrate various topographic maps of brain activity in accordance with the present invention.

Reference is now made to FIG. 3A, which illustrates the basic configuration of a topographic map 60 in accordance with the present invention. Map 60 is created by viewing brain 18 from a basal or inferior view along line 2—2 in the direction of arrow 62 as shown in FIG. 2B. The brain is then projected about line 6 shown in FIG. 2A. Portion 64 of map 60 contains points representative of signals sensed by sphenoidal electrode 72 in temporal region 48. Portion 66 contains points representative of signals sensed by sphenoidal electrode 74 illustrated in FIG. 2B in temporal region 44. Portion 68 contains points representative of signals sensed by electrodes placed on the subject's scalp in mid-line region 34. Portion 70 contains points representative of signals sensed by electrodes placed on the subject's scalp in mid-line region 30.

The basic map illustrated in FIG. 3A provides a number of advantages over the conventional topographic maps that use a top-down view as shown in FIG. 1. Brain activity occurring in the mesial temporal lobes and the lateral temporal lobes is represented near the center of the map, and thus, activity therefore can be more contiguously presented. Because the great majority of focal seizures, such as partial complex epileptic seizures, occur in the temporal lobes, a more diagnostically useful map is presented since the temporal lobe surfaces are contiguously represented. The basic quality of a topographic map in accordance with the present invention is displaying the temporal lobe activity including mesial temporal lobe activity from both halves of a brain adjacent to one another about center line 6. The mid-line regions of the brain are displayed adjacent the temporal lobe regions.

Figure 3B:
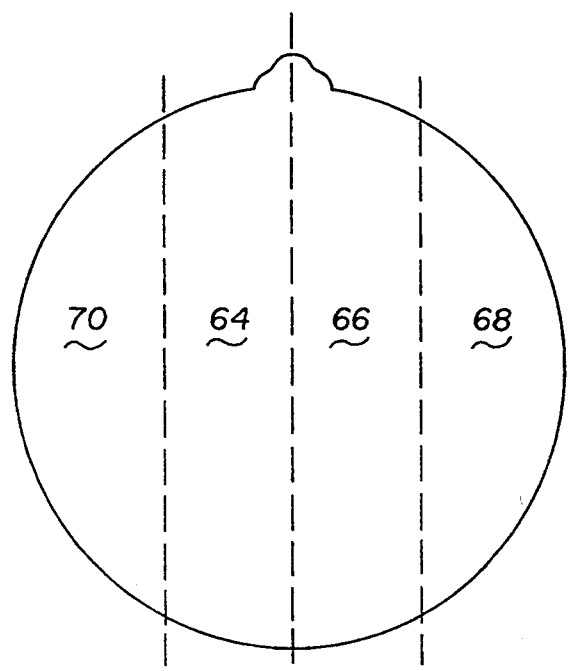
Figure 3C:
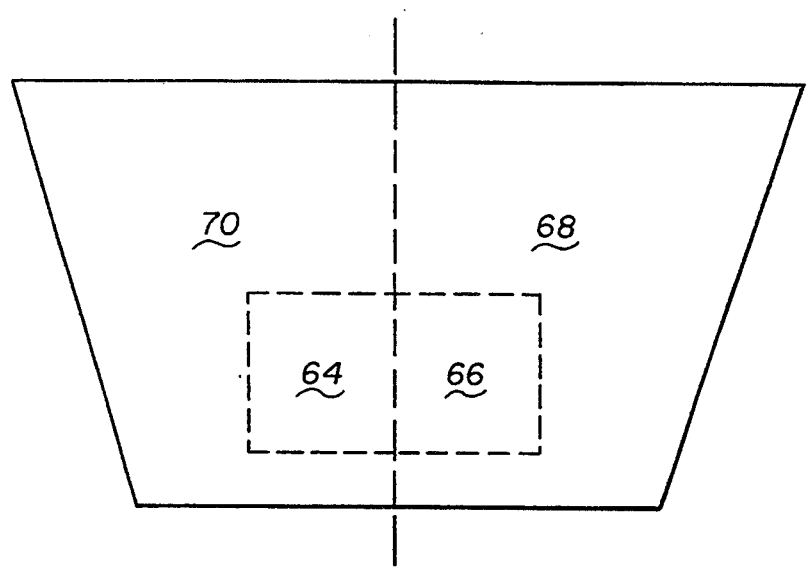
Figure 3D:
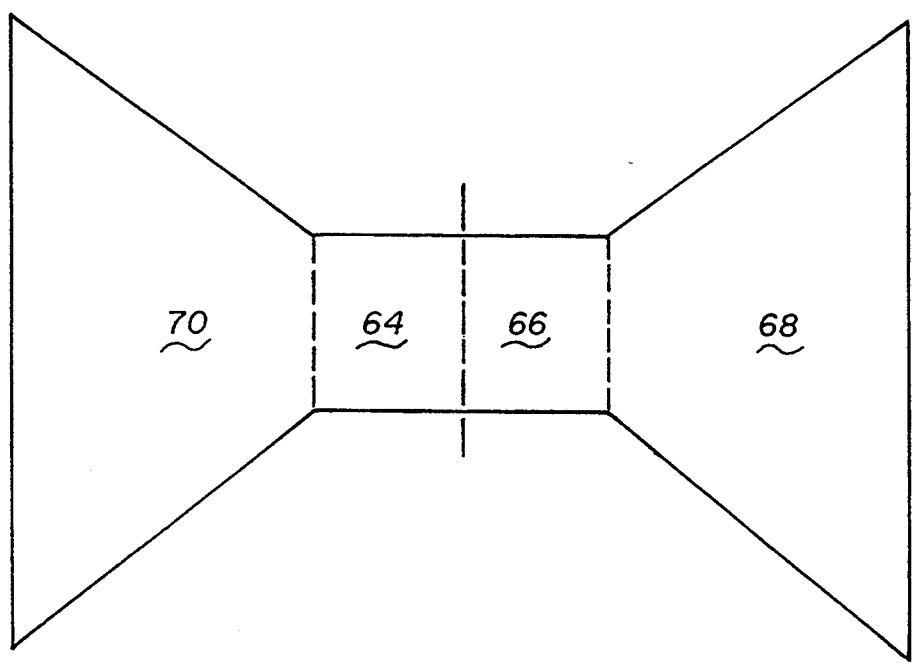

One skilled in the art will appreciate that the topographic map of present invention can be presented in a variety of forms while still retaining the advantages of the basic map of FIG. 3A. Referring to FIG. 3B, the topographic map can be reshaped so that it appears more like the conventional map of FIG. 1. If the map is generated using computer techniques, for example, the relative distances of the points representing signals sensed by the electrodes can be adjusted to present more roundness to the map. Referring to FIG. 3C, the size of portions 64 and 66 may be reduced and portions 68 and 70 reshaped so as to provide more diagnostic information and possibly ascertain relationships between brain activity in mid-line portion 70 and mid-line portion 68. FIG. 3D shows another example of the topographic map of the present invention in which portions 70 and 68 have been expanded with respect to portions 64 and 66. This type of map is useful where a large number of electrodes are used to sense brain activity in mid-line regions 30 and 34.

Figure 4:
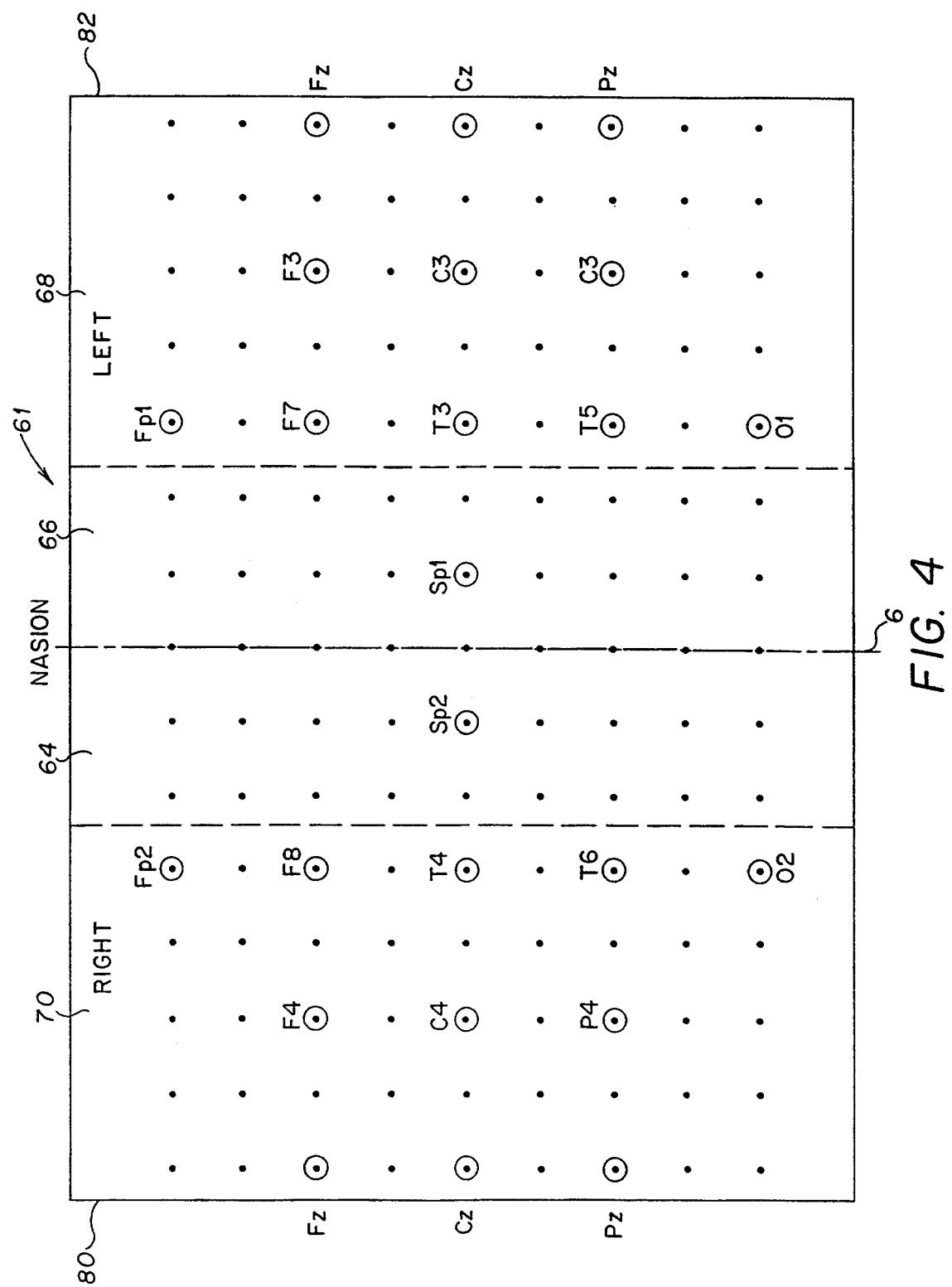
FIG. 4 illustrates a topographic map of FIG. 3A having the basic 10-20 electrode grid superimposed on the map and used to locate points of sensed electrical activity on the map.

Reference is now made to FIG. 4, which figure illustrates the basic topographic map 60 of FIG. 3A in combination with the International 10-20 Electrode Placement System. In the map 61 of FIG. 4, the 10-20 grid has been superimposed over portions 64, 66, 68, and 70 and the electrode designation characters are used to denote locations on the map. The combination of the 10-20 electrode placement system with the basal view mapping technique and the addition of the sphenoidal electrodes Sp1 and Sp2 provides a topographic map that is especially diagnostically useful and provides a number of advantages over conventional topographic maps. First, the very important map locations Sp1, Sp2 which represent signals sensed by sphenoidal electrodes 72 and 74 can be anatomically placed on the map as they are at the approximately 10-20 location with respect to the mid temporal electrodes T3 and T4 as well as to each other and the mid-line 6. In addition, the map is contiguous at the outer edges 80, 82 due to the dual placement of locations Fz, Cz and Pz that represent signals sensed by the mid-line electrodes. Thus, the entire surface of the brain is included and displayed on one contiguous plane in anatomically accurate and useful representation.

The basal view map of the present invention can be created easily using brain mapping equipment already available from a variety of manufacturers. Since most equipment presently on the market has the capability to draw a map as well as place identified points representing signals sensed by electrodes anywhere on the map, presentation of the basal view topographic map is a straight forward application of available display on output printing techniques. One skilled in the art will clearly recognize that the present invention involves a reorganization of data and therefore the mapping can be easily accomplished by modifying presently available software.

Figure 5:
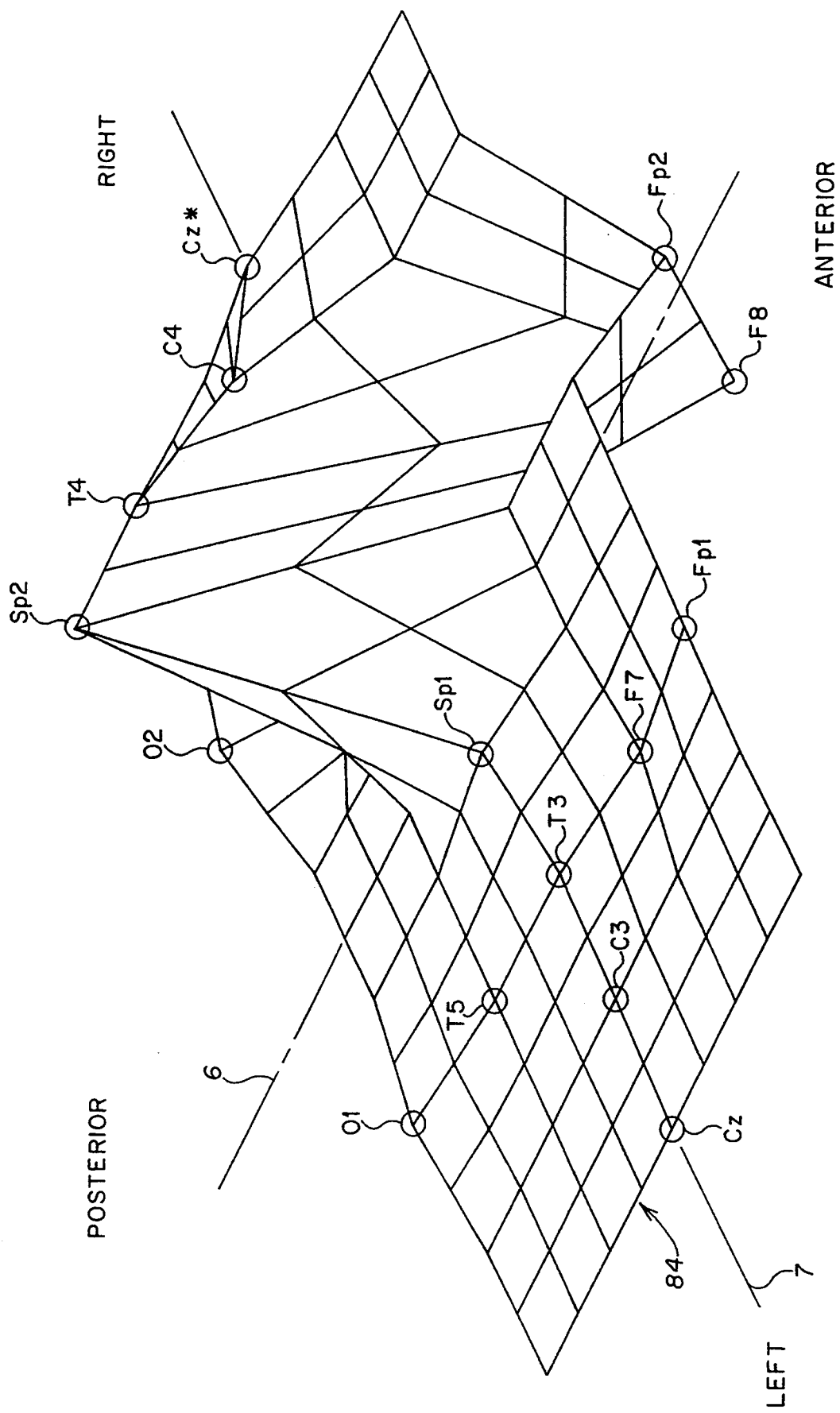
FIG. 5 illustrates a three dimensional topographic map of brain activity in accordance with the present invention based on the map of FIG. 3A.

Furthermore, three dimensional basal view mapping may be realized with the map and method of the present invention. Referring to FIG. 5, after the values of the electrical activity sensed by the electrodes have been determined, these values may be used in conjunction with a program, such as MathCAD (version 2.54), a readily available commercial software package into which raw numerical data can be imported for further processing by standard packaged algorithms. Math-CAD includes a three dimensional mapping algorithm, which was used to create the three dimensional map illustrated in FIG. 5. FIG. 5 illustrates a temporal lobe seizure centered about the right temporal lobe. In FIG. 5, each point denoted by an electrode designation character, corresponds to a value that determines the displacement from the plane 84 of the map representing a locus of points having a reference signal level. Points which have values above the reference signal level are displayed further away from the plane of the map than points having lesser values. For example, in FIG. 5 sphenoidal electrode sp2 had a value representing the peak of the sensed electrical activity. As also illustrated in FIG. 5, the three dimensional map can be bipolar as point F8 represents electrical activity having a negative value with respect to the reference plane 84. This type of presentation allows the physician to view the size and shape of the seizure, thus providing the physician with significant diagnostic information not previously available.

Figure 6:
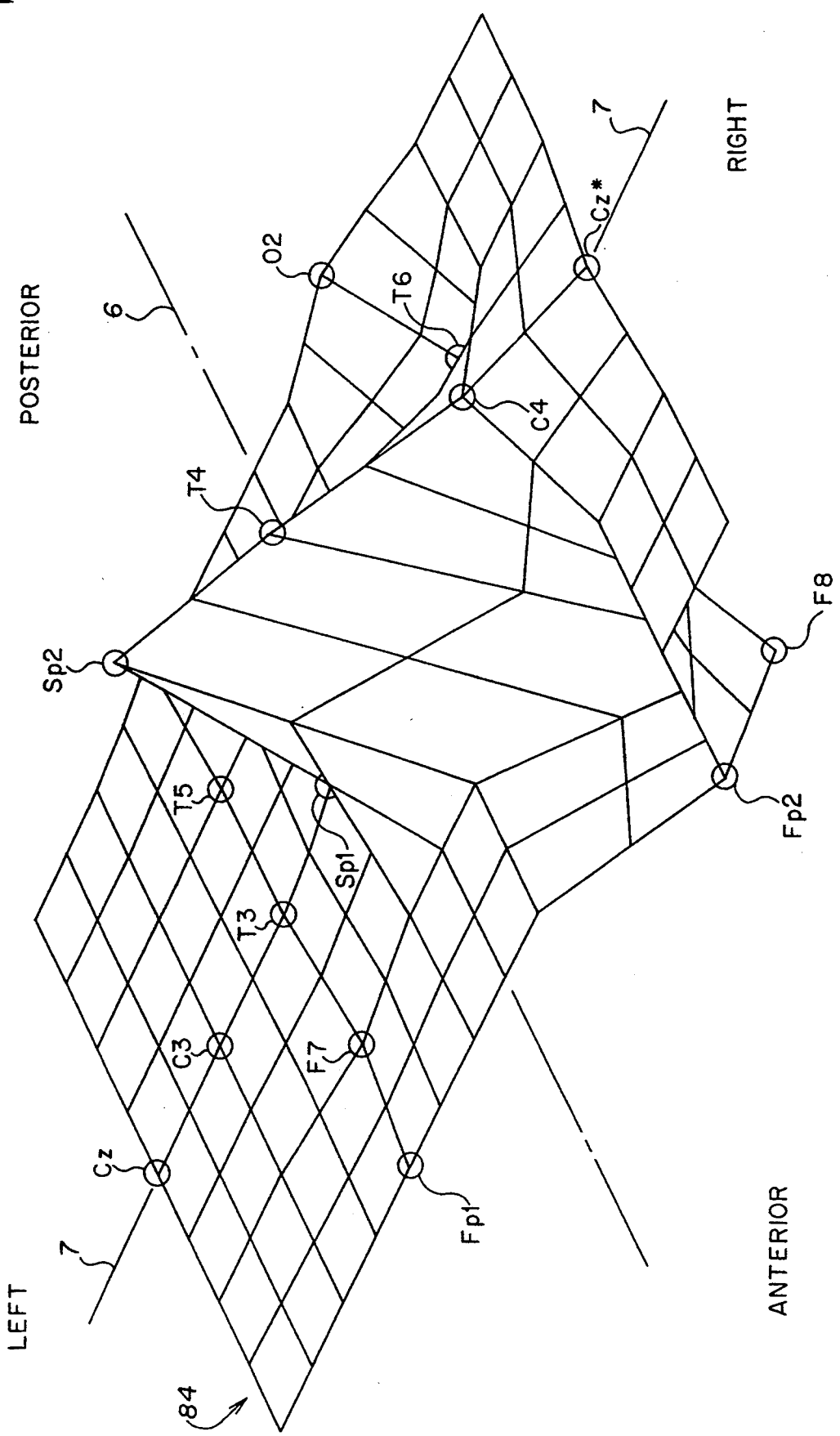
FIG. 6 illustrates the topographic map of FIG. 5, but rotated.

As illustrated in FIG. 6, the map in FIG. 5 can be rotated using a rotation algorithm available in the Math-CAD software package. In FIG. 5, the seizure was being viewed from left to right. By contrast, in FIG. 6, the three dimensional topographic map has been rotated such that the seizure can now be viewed from right to left. Thus, the overall shape, extent, and details of the peaks and valleys associated with the seizure can be inspected as well.

Figure 7:
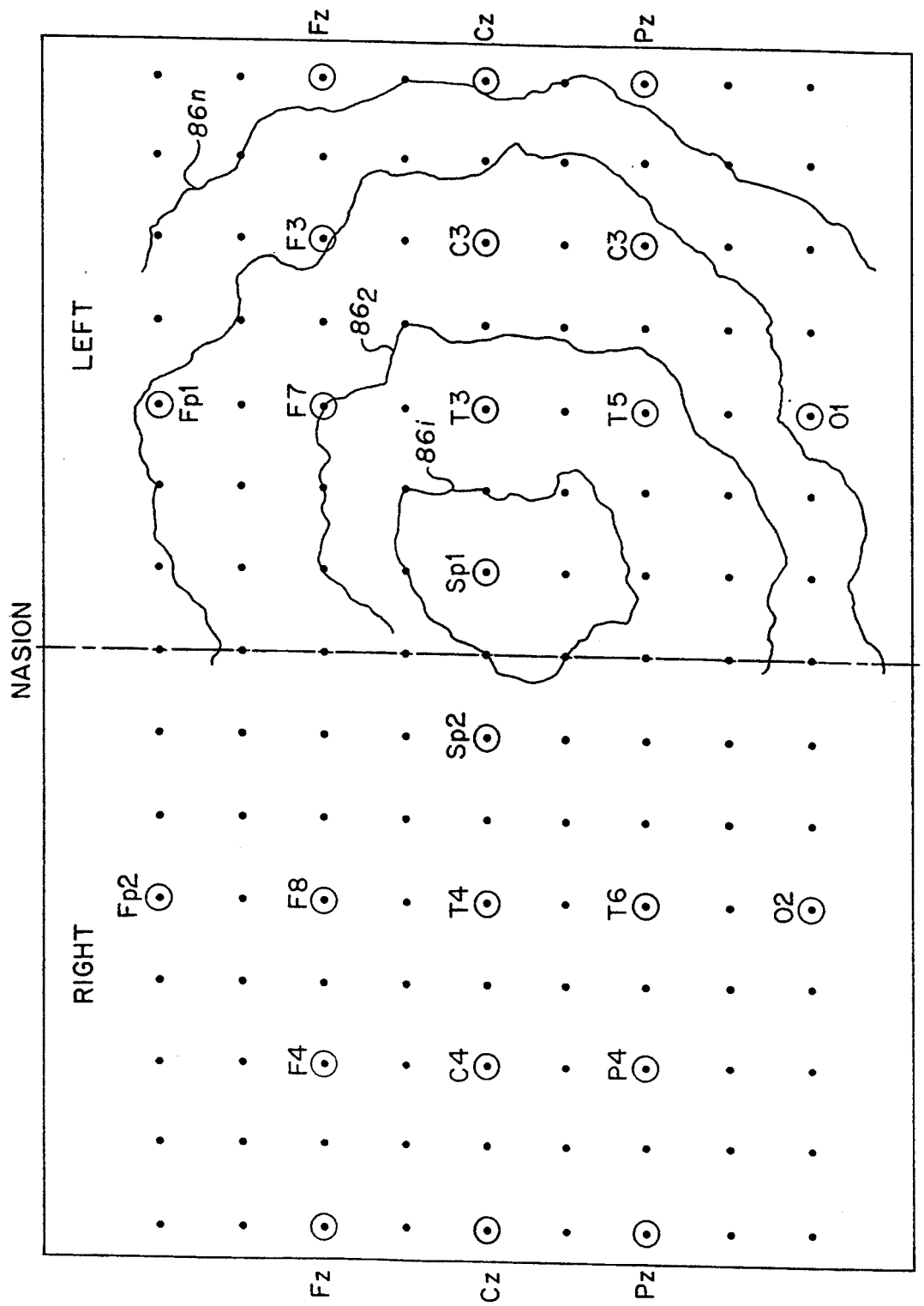
FIG. 7 illustrates the topographic map of FIG. 4 including contour lines connecting points on the map having substantially similar values.

Reference is now made to FIG. 7, which figure illustrates a two-dimensional version of the basal view map of the present invention incorporating points represented by the 10-20 electrodes. In the map of FIG. 7, contour lines $86i$, where i varies from 1-n are used to connect points on the map having substantially similar values. One skilled in the art will appreciate that instead of contour lines representing different voltage values on the map, the contours of a discharge could be represented by shades of gray or colors. The use of color is particularly helpful in representing the positive and negative variation of amplitudes with respect to the plane of the two-dimensional map.

The topographic map of the present invention and the method for mapping electrical activity such as discharges the basal view map may be used in a variety of brain mapping devices in the field of neurophysiology. For example, the topographic map and method of mapping of the present invention is useful to physicians in the fields of electroencephalography (EEG) evoked potential (EP) and electromagnetoencepholography (MEG). When used in conjunction with a portable discharge, sensing and recording system such as the Home Monitoring System available from Digitrace Care Services, Boston, Mass., the present invention may be used to provide additional information concerning ictal (actual discharge) and interictal (activity between discharges) events. The Home Monitoring System records data regarding ictal and interictal events. The recorded data may then be used to create the map of the present invention. A number of signals corresponding to waveforms within an ictal and/or interictal event, wherein each waveform represents an individual discharge, may be averaged together to provide data for mapping such that the map, particularly in the three dimensional version, more accurately represents the effect of the discharging epileptic surface as sensed by the sphenoidal electrodes to permit better visualization of the location and shape of the discharging epileptic surface. Averaging of signals over time tends to reduce noise and artifacts so that a more accurate picture of the discharge over time is obtained.

In addition, the basal view topographic map can be normalized to eliminate the amplitude difference caused by attenuation of the EEG signal in individual cases. One type of normalization is illustrated in FIGS. 5 and 6. The maximum discharge is seen at location Sp2, whose amplitude is used as the value for normalization. The amplitude at the maximum is set to be equal to one-half the distance on the grid from Cz to Cz along line 7. The amplitude of all other points may be then normalized proportionally to this peak value. An interpolating algorithm such as one available in the aforementioned program MathCAD may be used to generate required interpolated data. Normalization allows positive and negative discharges to be displayed on the map. Normalization eliminates the attenuation factors (specific attenuation of brain, bone, and skin, as well as attenuation due to tissue boundaries) that come in to play when a discharge occurs and an EEG is recorded on the scalp. Normalization thus permits qualified comparisons of the elements of the map between or among patients.

The basal view map and method of mapping of the present invention is useful for diagnosis of any kind of brain disorder, such as epilepsy, schizophrenia, Alzheimer's disease, dyslexia, and any memory disorder. The present invention may be used for functional mapping of brain activity or any kind of brain study. In the surgical treatment of focal epilepsy, the present invention can aid in the visualization of the necessary diagnostic information so that only the affected portion of the brain is removed during an operation.

Having thus described one particular embodiment of the invention, various alterations, modifications, and improvements will readily occur to those skilled in the art. For example, other extra-temporal or extra-frontal electrodes as identified in the International Electrode 10-20 Placement System could be used to provide additional data for the basal view map. In addition, other electrodes in addition to the sphenoidal electrodes such as so-called "mini-sphenoidals" could be used to measure brain activity on the mesial side of the temporal lobes and these additional signals could be incorporated into the basal view topographic map of the present invention. Such alterations, modifications, and improvements as are made obvious by this disclosure are intended to be part of this disclosure though not expressly stated herein, and are intended to be within the spirit and scope of the invention. Accordingly, the foregoing description is by way of example only and is not intended as limiting. The invention is limited only as defined in the following claims and equivalents thereto.

What is claimed is:

1. A graphic display of electrical activity of a brain comprising a first set of points representative of electrical activity occurring in a temporal region of a left brain hemisphere and a second set of points representative of electrical activity occurring in a temporal region of a right brain hemisphere displayed adjacent to one another and a third set of points representative of electrical activity occurring in a mid-line region of a left brain hemisphere and a fourth set of points representative of electrical activity occurring in a mid-line region of a right brain hemisphere displayed remote from one another wherein respective locations of the first and third set of points are displayed substantially as a mirror image of respective locations of the second and fourth sets of points; and a display for displaying the first, second, third, and fourth sets of points.

2. The graphic display of claim 1, wherein the first set of points and the second set of points are respectively derived from electrical activity sensed by at least one sphenoidal electrode disposed proximate a mesial temporal lobe.

3. The graphic display of claim 2, wherein the third set of points and the fourth set of points are derived from electrical activity sensed by a set of electrodes located according to an International 10–20 Electrode Placement System.

4. The graphic display of claim 3, further comprising a grid having uniformly spaced locations and wherein points in the first, second, third, and fourth sets of points are displayed at the uniformly spaced locations.

5. The graphic display of claim 3, wherein the first, second, third, and fourth sets of points are additionally displayed three dimensionally such that a value of an electrical discharge represented by a point determines a displacement from a plane of the display representing a locus of points having a reference signal level.

6. The graphic display system of claim 3, further comprising contour lines coupling points from the first, second, third, and fourth sets of points having substantially similar values.

7. The graphic display of claim 3, further comprising contours including respective shades of gray coupling points from the first, second, third, and fourth sets of points having respective predetermined ranges of values.

8. The graphic display of claim 3, further comprising contours including respective colors coupling points from the first, second, third, and fourth sets of points having respective predetermined ranges of values.

9. The graphic display of claim 3, wherein values of points in the first, second, third, and fourth sets of points are normalized with respect to a reference value.

10. The graphic display of claim 9, wherein the reference value is a length of the map from a first set of mid-line points to a second set of mid-line points.

11. A topographic map of electrical discharges occurring in a brain, comprising:

a first set of points representative of electrical discharges occurring in a mesial temporal region of a left brain hemisphere and second set of points representative of electrical discharges occurring in a mesial temporal region of a right brain hemisphere being located adjacent on the topographic map; and a third set of points representative of electrical discharges occurring in a mid-line region of a left brain hemisphere and a fourth set of points representative of electrical discharges occurring in a mid-line region of a right brain hemisphere being located adjacent the first and second set of points, respectively; and a display for displaying the first, second, third, and fourth sets of points.

12. The topographic map of claim 11, wherein the first set of points and the second set of points are respectively derived from electrical discharges sensed by at least one sphenoidal electrode disposed proximate a mesial temporal lobe.

13. The topographic map of claim 12, wherein the third set of points and the fourth set of points are derived from electrical discharges sensed by a set of electrodes located according to an International 10–20 Electrode Placement System.

14. The topographic map of claim 12, further comprising a grid having uniformly spaced locations and wherein points in the first, second, third, and fourth sets of points are disposed at the uniformly spaced locations.

15. The topographic map of claim 12, wherein the first, second, third, and fourth sets of points are additionally located three dimensionally such that a value of an electrical discharge represented by a point determines a displacement from a plane of the map representing a locus of points having a reference signal level.

16. The topographic map of claim 12, further comprising contour lines coupling points from the first, second, third, and fourth sets of points having substantially similar values.

17. The topographic map of claim 12, further comprising contours including respective shades of gray coupling points from the first, second, third, and fourth sets of points having respective predetermined ranges of values.

18. The topographic map of claim 12, further comprising contours including respective colors coupling points from the first, second, third, and fourth sets of points having respective predetermined ranges of values.

19. The topographic map of claim 12, wherein values of points in the first, second, third, and fourth sets of points are normalized with respect to a reference value.

20. The topographic map of claim 19, wherein the reference value is a length of the map from a first set of mid-line points to a second set of mid-line points.

21. A method for mapping electrical activity occurring in a brain, comprising the steps of:

locating a first set of points representative of electrical activity occurring in a mesial temporal region of a left brain hemisphere and a second set of points representative of electrical activity occurring in a mesial temporal region of a right brain hemisphere adjacent on a topographic map; and locating a third set of points representative of electrical activity occurring in a mid-line region of a left brain hemisphere and a fourth set of points representative of electrical activity occurring in a right brain hemisphere respectively adjacent the first and second set of points on the topographic map.

22. The method of claim 21, further comprising the steps of:

sensing electrical activity using at least one sphenoidal electrode disposed proximate a left mesial temporal lobe and at least one sphenoidal electrode disposed proximate a right mesial temporal lobe; and respectively deriving the first and second sets of points from the sensed electrical activity.

23. The method of claim 22, further comprising the steps of:

sensing electrical activity using a first set of electrodes located according to an International 10–20 Electrode Placement System; and deriving the third and fourth sets of points from the electrical activity sensed by the first set of electrodes.

24. The method of claim 23, further comprising the step of averaging signals corresponding to a plurality of waveforms within an ictal event, each waveform representing an individual discharge sensed by the at least one sphenoidal electrode and the first set of electrodes and deriving the first, second, third, and fourth sets of points from the averaged signals.

25. The method of claim 24, further comprising the step of averaging signals corresponding to a plurality of waveforms within an interictal event, each waveform representing an individual discharge sensed by the at least one sphenoidal electrode and the first set of electrodes and deriving the first, second, third, and fourth sets of points from the average of the signals corresponding to the plurality of ictal events and the signals corresponding to the plurality of interictal events.

26. The method of claim 23, further comprising the step of locating the first, second, third, and fourth sets of points three dimensionally on the map such that a value of electrical activity represented by a point determines a displacement from a plane of the map representing a locus of points having a reference signal level.

* * * * *